United States Patent [19]

Akagi et al.

[11] Patent Number: 5,723,269
[45] Date of Patent: *Mar. 3, 1998

[54] MICROPARTICLE PREPARATION AND PRODUCTION THEREOF

[75] Inventors: Yasaburo Akagi, Takatsuki; Nobuyuki Takechi, Osaka; Muneo Nonomura, Suita, all of Japan

[73] Assignee: Takeda Chemical Industries, Ltd., Osaka, Japan

[*] Notice: The term of this patent shall not extend beyond the expiration date of Pat. No. 5,622,657.

[21] Appl. No.: 612,071

[22] Filed: Mar. 7, 1996

Related U.S. Application Data

[63] Continuation of Ser. No. 95,765, Jul. 23, 1993, abandoned.

[30] Foreign Application Priority Data

Jul. 24, 1992 [JP] Japan ................... 4-198242
Feb. 9, 1993 [JP] Japan ................... 5-021142

[51] Int. Cl.⁶ ........................................ A61K 9/58
[52] U.S. Cl. ............ 424/497; 424/489; 264/432; 264/46; 428/402.21; 514/963
[58] Field of Search ................. 424/489, 487; 264/432, 46; 428/402.21; 514/963

[56] References Cited

U.S. PATENT DOCUMENTS

| | | | |
|---|---|---|---|
| 4,486,435 | 12/1984 | Schmidt et al. | 424/252 |
| 4,652,441 | 3/1987 | Okada et al. | 424/19 |
| 4,675,189 | 6/1987 | Kent et al. | 424/490 |
| 4,711,782 | 12/1987 | Okada et al. | 424/455 |
| 4,954,298 | 9/1990 | Yamamoto et al. | 264/46 |
| 5,061,492 | 10/1991 | Okada et al. | 424/423 |
| 5,271,945 | 12/1993 | Yoshioka et al. | 424/489 |

FOREIGN PATENT DOCUMENTS

| | | |
|---|---|---|
| 315875 | 5/1989 | European Pat. Off. . |
| 505966 | 9/1992 | European Pat. Off. . |
| 535937 | 4/1993 | European Pat. Off. . |
| 3916020 | 11/1990 | Germany . |

OTHER PUBLICATIONS

Remingtons Pharmaceutical Suemes pp. 1630–1631 (1985).
*Journal of Pharmacy and Pharmacology*, 1988, vol. 40, pp. 754–757.

*Primary Examiner*—Jyothsan Venkat
*Attorney, Agent, or Firm*—Foley & Lardner

[57] ABSTRACT

A novel microparticle preparation comprising microparticles of a polymer which contain a drug and are at least partially or wholly coated with a water-soluble inorganic salt, a water-soluble organic acid or a water-soluble salt of an organic acid, which acts as an agent for preventing aggregation of the microparticle preparation is disclosed. The preparation is produced by spraying a polymer solution containing a drug and a solution or dispersion of a water-soluble inorganic salt, a water-soluble organic acid or a water-soluble salt of an organic acid from different nozzles and contacting them with each other in a spray dryer. In this procedure, if desired, a non-ionic surfactant may be added to the solution of the water-soluble inorganic salt, the water-soluble organic acid or the water-soluble salt of organic acid, or a solution of non-ionic surfactant may be sprayed from the other nozzle simultaneously.

28 Claims, No Drawings

5,723,269

MICROPARTICLE PREPARATION AND PRODUCTION THEREOF

This application is a continuation of application Ser. No. 08/095,765, filed Jul. 23, 1993 now abandoned.

FIELD OF THE INVENTION

The present invention relates to a microparticle preparation comprising microparticles of a polymer which contain a drug and are at least partially or wholly coated with an inorganic salt, an organic acid or a salt of organic acid for preventing aggregation of the microparticles (hereinafter sometimes referred to as a microparticle preparation) and the production thereof by spray drying.

BACKGROUND OF THE INVENTION

The traditional microcapsulation method which comprises formation of a three-phase emulsion containing a drug, followed by microcapsulation thereof by in-water drying process to obtain microcapsules is mentioned in JP-A-60-100516 (U.S. Pat. No. 4,652,441). Although this technique improves the above disadvantage of adhesion, some points to be improved still remain. Namely, it is difficult to obtain microcapsules having a high drug content because, in the case of a water-soluble, drug the drug leaks out to the outer aqueous phase and the entrapping ratio thereof drops. Further, in general, the microcapsules thus obtained have a large initial release rate of a drug. Furthermore, the microcapsules tend to be readily influenced by scaling up of the production and large scale treatment is difficult.

On the other hand, there are reports relating to microparticles produced by spray drying with one nozzle. However, in any of these reports, the initial release of a drug, so called initial burst of a drug from the microparticles, is large and the desired prolonged release over a long period of time is not achieved. Further, the time which is needed to disperse the microparticles completely and uniformly is to be improved. Furthermore, there is a problem that a large amount of microparticles often aggregate to each other and adhere to a spray dryer.

SUMMARY OF THE INVENTION

Under these circumstances, the present inventors have intensively studied to develop water-soluble or fat-soluble microparticle preparations, including microcapsules, having a lower aggregation or adhesion property, and a good dispersibility. As a result, it has been found that microparticle preparation, including microcapsules and microspheres, having a high entrapping ratio of a drug, a small initial burst of a drug and excellent properties can be obtained efficiently and continuously in a large amount in a short period of time by atomizing and spraying (1) a solution containing a drug and a polymer, (2) a dispersion solution in which a part or whole of a drug or polymer is in a solid state, (3) an O/W, W/O, W/O/W or O/W/O type emulsion comprising a solution containing a drug and/or a polymer or (4) an O/W, W/O, W/O/W or O/W/O type emulsion comprising a dispersion solution in which a part or whole of a drug or a polymer is in a state of dispersion from one nozzle of a spray dryer (two-fluid nozzle, multi-fluid nozzle, pressure nozzle or rotary disc for two or more-liquid spraying), and by spraying the a solution of a non-adhesive water-soluble inorganic salt, organic acid or salt of organic acid, as an agent for preventing aggregation of microparticle preparation,including microcapsules and microsphere, from the other nozzle. Said solution of the inorganic salt, organic acid or salt of the organic acid may be in the form of a suspension thereof.

Further, it has been found that microparticle preparation, including microcapsules and microsphere, having a good dipersibility can be obtained by (1) spraying a solution containing a non-ionic surfactant in addition to the inorganic salt, organic acid or salt of the organic acid or (2) further spraying a solution containing a non-ionic surfactant and the solution containing the inorganic salt, organic acid or salt of the organic acid simultaneously.

After further studies based on this findings, the present invention has been completed.

The present invention provides a microparticle preparation comprising microparticles of a polymer which contain a drug and are at least partially or wholly coated with an inorganic salt, an organic acid or a salt of an organic acid.

Further, the present invention provides a process for the production of a microparticle preparation comprising spraying a solution of a polymer containing a drug and a solution of a water-soluble inorganic salt, organic acid or salt of an organic acid separately from different nozzles and contacting them with each other in a spray dryer to produce microparticles of the polymer which contain the drug and are at least partially or wholly coated with the inorganic salt, the organic acid or the salt of the organic acid.

In the above production of microparticle preparation of this invention, a microparticle preparation having a good dipersibility can be obtained by (1) spraying a solution containing a non-ionic surfactant in addition to the inorganic salt, organic acid or salt of the organic acid or (2) further spraying a solution containing a non-ionic surfactant and the solution containing the inorganic salt, organic acid or salt of the organic acid simultaneously.

According to the present invention, it is possible to produce a microparticle preparation having a desired and strong structure with minimizing loss of a drug by spray-drying the solution, emulsion or suspension containing a drug and a polymer by using a spray dryer to volatilize water as well as an organic solvent in a moment. Further, it is possible to reduce the initial burst of a drug to a smaller amount than that of the in-water drying process. Furthermore, it is possible to obtain powder particles having excellent fluidity in a short period of time without employing any freeze-drying step by spray the solution of the inorganic salt, the organic acid or the salt of the organic acid from another nozzle at the same time to coat at least partially or wholly the surface of the microparticle with the inorganic salt, organic acid or salt of the organic acid, thereby preventing aggregation of the microparticles to each other and adhesion of the microparticles to a spray dryer. In addition to the foregoing, a microparticle preparation having a good dipersibility can be obtained by (1) spraying a solution containing a non-ionic surfactant in addition to the inorganic salt, organic acid or salt of the organic acid or (2) further spraying a solution containing a non-ionic surfactant and the solution containing the inorganic salt, organic acid or salt of the organic acid simultaneously.

DETAILED DESCRIPTION OF THE INVENTION

An example of the microparticle preparation includes microcapsules and the like. Most preferred examples include a microcapsule.

The drug to be used in the present invention is not specifically limited. Examples thereof include peptides having biological activities, other antibiotics, antitumor agents, antipyretics, analgestics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone agents, narcotic antagonists, bone resorption inhibitors, angiogenesis inhibiting substances and the like.

Among these drugs, preferred examples include peptides having biological activities, bone resorption inhibitors and angiogenesis inhibiting substances.

The peptides having biological activities to be used in the present invention are those having two or more amino acids, preferably having a molecular weight of about 200 to 80,000.

Examples of the peptide include luteinizing hormone-releasing hormone (LH-RH) and, its derivatives having similar acitivity, i.e., a peptide of the formula (I):

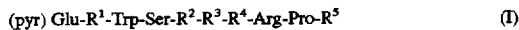

(pyr) Glu-R$^1$-Trp-Ser-R$^2$-R$^3$-R$^4$-Arg-Pro-R$^5$  (I)

wherein R$^1$ is His, Tyr, Trp, or p-NH$_2$-Phe; R$^2$ is Tyr or Phe; R$^3$ is Gly or D-amino acid residues; R$^4$ is Leu, Ile or Nle; and R$^5$ is Gly-NH-R$^6$ (wherein R$^6$ is H or lower alkyl optionally substituted with hydroxyl) or NH-R$^6$ (wherein R$^6$ is as defined above), or a salt thereof [see, U.S. Pat. Nos. 3,853,837, 4,008,209 and 3,972,859; G.B. Patent No. 1,423,083; and Proc. Nat. Acad. Sci. U.S.A., vol. 78, pp. 6509–6512 (1981)].

As the D-amino acid residue represented by R$^3$ in the above formula (I), there are, for example, α-D-amino acids having up to 9 carbon atoms [e.g., D-(Leu, Ile, Nle, Val, NVal, Abu, Phe, Phg, Ser, Tyr, Met, Ala, Trp, α-Aibu, etc.), etc] and the like. These residues may have suitable propective groups (e.g., t-butyl, t-butoxy, t-butoxycarbonyl, etc). The acid addition salts and metal complexes of the peptide of the formula (I) [hereinafter referred to as the peptide (I)] can be used in the same manner as the peptide (I).

The abbreviation of amino acids, peptides, protective groups, etc. in the peptide (I) are those establised by IUPAC-IUB Commission on Biochemical Nomenclature or those commonly used in the art. When optical isomers of amino acids are present, the amino acids are represented as L-isomers unless otherwise indicated.

In the present specification, the acetic acid salt of the peptide (I) [wherein R$^1$ is His, R$^2$ is Tyr, R$^3$ is D-Leu, R$^4$ is Leu and R$^5$ is NHCH$_2$—CH$_3$] is referred to as "TAP-144".

Examples of the peptide (I) include LH-RH antagonists (see U.S. Pat. Nos. 4,086,219, 4,124,577, 4,253,997 and 4,317,815).

Further examples of the peptides having biological acitvities include oligopeptides such as insulin, somatostatin, somatostatin deruvatives (see U.S. Pat. Nos. 4,087,390, 4,093,574, 4,100,117 and 4,253,998), growth hormone, prolactin, adrenocorticotropic hormone (ACTH), melanocyte-stimulating hormone (MSH), thyrotropin-releasing hormone (TRH), their salts and derivatives (see JP-A 50-121273 and JP-A 52-116465), thyroid-stimulating hormone (TSH), luteinizing hormone (LH), follicle-stimulation hormone (FSH), vasopressin, vasopressin derivatives {desmopressin [see Folia Endocrinologica Japonica, vol. 54, No. 5, pp. 676–691 (1978)]}, oxytocin, calcitonin, parothyroid hormone, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277, 394 and EP-A 31,567); and polypeptides such as endorphin, kyotorphin, interferon (α-type, β-type, γ-type), interleukin (I to XI), tuftsin, thymopoietin, tymosin, thymosthymlin, thymic hormone factor (THF), serum thymic factor (FTS) and derivatives thereof (see U.S. Pat. No. 4,299,438) and other thymic factors [see Medicine in Progerss, vol. 125, No. 10, pp. 835–843 (1983)], tumor necrosis factor TNF), colony stimulating factor (CSF), motilin, deinorphin, bombesin, neurotensin, caerulein, bradykinin, urokinase, asparaginase, kallikrein, substance P, nerve growth factor, blood coagulation factor VIII and IX, lysozyme chloride, polymyxin B, colistin, gramicidin, bacitracin, protein synthesis-stimulating peptide (see G.B. Patent No. 8,232,082), gastric inhibitory polypeptide (GIP), vasoactive intestinal polypeptide (VIP), platelet-derived growth factor (PDGH), growth hormone-releasing factor (GRF, somatoclinine), bone morphagenetic protein (BMP), epidermal growth hormone (EGF) and the like.

Examples of the above antitumor agent include bleomycin hydrochloride, methotrexate, actinomycin D, mitomycin C, vinblastine sulfate, vincristine sulfate, daunorubicin hydrochloride, adriamynin, neocarzinostatin, cytosine arabinoside, fluorouracil, tetrahydrofuryl-5-fluorouracil, picibanil, lentinan, levamisole, bestatin, azimexon, glycyrrhizin, poly A:U, poly ICLC and the like.

Examples of the above atibiotics include gentamicin, dibekacin, kanendomycin, lividomycin, tobromycin, amikacin, fradiomycin, sisomysin, tetracycline, oxytetracycline, roliteracycline, doxycycline, ampicillin, piperacillin, ticarcillin, cefalotin, cefaloridine, cefotiam, cefsulodin, cefmenoxime, cefmetazole, cefazollin, cefataxim, cefoperazone, ceftizoxime, moxolactame, thienamycin, sulfazecine, azusleonam, salts thereof, and the like.

Examples of the above antipyretic, analgesic and anti-inflammatory agent include salicylic acid, sulpyrine, flufenamic acid, diclofenace, indometacin, morphine, pethidine, levorphanol tertrate, oxymorphone and the like.

Examples of the antitussive expectorant include ephedrine, methylephedrine, noscapine, codeine, dihydrocodeine, alloclamide, chlorphezianol, picoperidamine, cloperastine, protokylol, isoproterenol, salbutamol, terebutaline, salts thereof and the like.

Examples of the sedative include chlorpromazine, prochloperazine, trifluoperazine, atropine, scopolamine, salts thereof and the like.

Examples of the muscle relaxant include pridinol, tubocurarine, pancuronium and the like.

Examples of the antiepileptic agent include phenytoin, ethosuximide, acetazolamide, chlordiazepoxide and the like.

Examples of the antiulcer agent include metoclopramide, histidine and the like.

Examples of the antidepressant include imipramine, clomipramine, onxiptiline, phenelzine and the like.

Examples of the antiallergic agent include diphenhydramine hydrochloride, chlorpheniramine malate, tripelennamine hydrochloride, methdilazine hydrochloride, clemizole hydrochloride, diphenylpyraline hydrochloride, methoxyphenemine hydrochloride and the like.

Examples of the cardiotonic include transpieoxocamphor, terephylol, aminophylline, etilifrine and the like.

Examples of the antiarrythmic agent include propranolol, alprenolol, bufetololoxyprenolol and the like.

Examples of the vasodilator include oxyfedrine, diltiazem, tolazoline, hexobendine, bamethan and the like.

Examples of the hypotensive diuretic include hexamethonium bromide, pentolinium, mecamylamine, ecarazine, clonidine and the like.

Examples of the antidiabetic agent include glymidine, glipizide, phenformin, buformin, metformin and the like.

Examples of the anticoagulant include heparin, citric acid and the like.

Examples of the hemostatic include thromboplastin, thrombin, menadione, acetomenaphthone, ε-aminocaproic acid, tranexamic acid, carbazochrome sulfonate, adrenochrome monoaminoguanidine and the like.

Examples of the antituberculous agent include isoniazid, ethambutol, para-aminosalicylic acid and the like.

Examples of the hormones agents include prednisolone, dexamethasone, betametasone, hexoestrol, methymazole and the like.

Examples of the narcotic antagonist include levallorphan, nalorphine, naloxone, salts thereof and the like.

Examples of the bone resoption inhibitors include (sulfur-containing alkyl) aminomethylenebisphosphonic acid and the like.

Examples of the angiogenesis-inhibiting substance include angiostatic steroid [Science, 221, 719 (1983)], fumagillin (e.g., EP-A-325199, etc.), fumagillol derivatives (e.g., EP-A- 357061, EP-A-359036, EP-A-386667, EP-A-415294, etc.) and the like.

Among these drugs, this invention can be preferably applicable to a water-soluble drug, since a water-soluble drug is apt to be released excessively at the initial stage of administration.

A solubility in water of the water-soluble drug of the present invention depends on an n-octanol/water partition coefficient.

In the present invention, an n-octanol/water partition coefficient of the water-soluble drug is preferably not more than 1, more preferably not more than 0.1.

The n-octanol/water partition coefficient can be determined by the method described in Robert E. Notari, "Biepharmaceutics and Pharmacokinetics", Marcel Dekker Inc., 1975, New York, U.S.A. Thus, equal amounts of n-octanol and a buffer solution (pH 5.5) are placed in a test tube to give a 1:1 mixture. The buffer solution is exemplified by Sörensen buffer [Engebniss der Physiology 12, 393 (1912)], Clark-Lubs buffer [Journal of Bacteriology 2, (1), 109, 191 (1971)], MacIlvaine buffer [Journal Biological Chemistry 49, 183 (192)], Michelis buffer [Die Wasser-Stoffionekonzentration, p. 186 (1914)], Kolthoff buffer [Biochemische Zeitschrift 179, 410 (1926)] and so on. An adequate amount of the drug to be tested is added to the mixture, and the test tube is stoppered, immersed in a constant-temperature bath (25° C.) and shaken vigorously. When it appears that the drug has been dissolved in between both the liquid layers and an equilibrium has been reached, the mixture is allowed to stand or is centrifuged, and aliquots of the upper and lower liquid layer are pipeted separately and analyzed for the concentration of the drug in each layer. The ratio of the concentration of the drug in the n-octanol layer to the concentration of the drug in the aqueous layer is the n-octanol/water partition coefficient.

These drugs themselves and their pharmaceutically acceptable salts can be used in the present invention.

Examples of the pharmaceutically acceptable salts of the drugs include a salt with an inorganic acid (e.g., hydrochloric acid, sulfulic acid, nitric acid, etc.) a salt with an organic acid (e.g., carbonic acid, citric acid, etc.), when the drug has a basic residue such as an amino group and so on. Examples of the pharmaceutically acceptable salts of the drugs include a salt with an inorganic base (e.g., alkaline metal such as sodium, potassium and so on), organic basic compound (e.g., triethylamine, pyridine, etc.), basic amino acid (e.g., arginine, histidine, etc.) and so on, when the drugs have an acidic residue such as carboxyl group and so on.

The amount of the above drugs to be used depends on a particular kind of drug, desired pharmacological activity, duration time and the like. The concentration of the drugs in the solution to be sprayed, for example, is about 0.001% to about 70% (W/W), preferably about 0.01% to about 50% (W/W).

The polymer in the present invention is slightly water-soluble or water-insoluble, and has biocompatibility. "Slightly water-soluble" means that solubility of the polymer in water is not exceeding about 3% (W/W).

The amount of the polymer to be used depends on a particular strength of the pharmacological activity of the drug, release rate and period of the drug and the like. For example, the polymer is used in an amount of 0.5 to 1,000 times the weight of the drug. Preferably, the polymer in an amount of about 1 to 100 times the weight of the drug is used.

The weight-average molecular weight of the polymer to be used may be selected from the range of about 3,000 to 30,000, preferably about 5,000 to 25,000, more preferably about 5,000 to 20,000.

The dispersity of the polymer to be used may be selected from the range of about 1.2 to 4.0, preferably about 1.5 to 3.5, more preferably about 1.5 to 2.5.

The weight-average molecular weight and dispersity of the polymer in the present specification are determined by gel permeation chromatography (GPC) in terms of polystyrene as a standard. In the determination, GPC column KF804×2 (Shyowa-denko, Japan) is used and chloroform is used as a mobile phase.

Examples of the polymer in the present invention include biodegradable polymers such as poly fatty acid esters [e.g., homopolymer of fatty acid (e.g., polylactic acid, polyglycolic acid, polycitric acid, polymalic acid, etc.) or copolymers of two or more fatty acids (e.g., copolymer of lactic acid/glycolic acid, copolymer of 2-hydroxybytyric acid/glycolic acid, etc.), a mixture of the homopolymer and/or copolymer (e.g., mixture of poly lactic acid and copolymer of 2-hydroxybytyric acid/glycolic acids, etc.), examples of the fatty acid include α-hydroxycarboxylic acids (e.g., glycolic acid, lactic acid, 2-hydroxybutyric acid, 2-hydroxyvaleric acid, 2-hydroxy-3-methylbytyric acid, 2-hydroxycaproic acid, 2-hydroxyisocaproic acid, 2-hydroxycaprylic acid, etc.), cyclic dimers of α-hydroxycarboxylic acids (e.g., glycolide, lactide, etc.), hydroxydicarboxylic acid (e.g., malic acid, etc.), hydroxytricarboxylic acid (e.g., citric acid, etc.) and so on], poly-α-cyanoacrylate, polyalkylene oxyalates (e.g., polytrimethylene oxyalate, polyteteramethylene oxyalate, etc.), poly ortho esters, poly ortho carbonates and other polycarbonates (e.g., polyethylene carbonate, polyethylenepropylene carbonate, etc.), polyamino acids (e.g., poly-γ-benzyl-L-glutamic acid, poly-L-alanine, poly-γ-methyl-L-glutamic acid, etc.) and the like. Further examples of the biocompatible polymers include polyacrylic acid, polymethacrylic acid, copolymer of acrylic acid and methacrylic acid, silicon polymer, dextransterarate, ethylcellulose, acetylcellulose, maleic anhydride copolymers, ethylene-vinylacetate copolymers, polyvinyl acetate, polyvinyl alcohol, polyacrylamide and the like. These polymers may be used alone or in combination thereof. They may be used in the form of a copolymer or mere mixture of these two or more polymers. They may be in the form 15 of salts thereof. Among these polymers, in particular, poly fatty acid esters, poly-α-cyanoacrylate are preferred. Most preferred examples include poly fatty acid esters.

Among these poly fatty acid esters, in particular, homopolymers of α-hydroxycarboxylic acids, cyclic dimers of α-hydroxycarboxylic acids; copolymers of two or more α-hydroxycarboxylic acids, cyclic dimers of α-hydroxycarboxylic acids; and a mixture of the homopolymers and/or the copolymers are preferred. More preferred examples include homopolymers of α-hydroxycarboxlic acids; copolymers of two or more α-hydroxycarboxylic acids; and a mixture of the homopolymers and/or the copolymers. Most preferred examples include polylactic acid, copolymer of lactic acid/glycolic acid, copolymer of 2-hydroxybutyric acid/glycolic acid and a mixture thereof.

When these α-hydroxycarboxylic acids, cyclic dimers of α- hydroxycarboxylic acids, hydroxydicarboxylic acids, hydroxytricarboxylic acids may be D-, L- or D,L-configured, the D-, L- and D,L-compounds can be used equally.

When a copolymer of lactic acid/glycolic acid is used as one example of the above polymer, its composition (monomer) ratio is preferably about 100/0 to 50/50 (mole/mole). When a copolymer of 2-hydroxybutyric acid/glycolic acid is used as one example of the above polymer, its composition (monomer) ratio is preferable about 100/0 to 25/75 (mole/mole).

The weight-average molecular weight of the copolymer of lactic acid/glycolic acid is preferably about 3,000 to 30,000, more preferably about 5,00 to 20,000.

When a mixture of a polylactic acid (A) and a copolymer of 2-hydroxybutyric acid/glycolic acid (B) is used as one example of the above polymers, the mixture can be used in a blend ratio of about 10/90 to 90/10 (by weight), preferably about 25/75 to 75/25 (W/W).

The weight-average molecular weight of the polylactic acid (A) is preferably about 3,000 to 30,000, more preferably about 5,000 to 20,000.

The preferred proportion of glycolic acid in the copolymer (B) is in the range of about 40 to 70 mole %.

The weight-average molecular weight of the copolymer (B) is preferably about 5,000 to 25,000, more preferably about 5,000 to 20,000.

As the water-soluble inorganic salt, the organic acid or the salt of organic acid, which is used as an aggregation-preventing agent in the present invention, there can be used water-soluble materials which are applicable to human, solid at room temperature (about 15° to 25° C.) and non-adhesive in their dried state.

Examples of the water-soluble inorganic salts include halogenated alkali metal (e.g., sodium chloride, potassium chloride, sodium bromide, potassium bromide, etc.), halogenated alkali-earth metal (e.g., calcium chloride, magnesium chloride, etc.), halogenated ammonium (e.g., ammonium chloride, ammonium bromide, etc.), alkali metal carbonate or alkali metal hydrogencarbonate (e.g., sodium carbonate,potassium carbonate, sodium hydrogen carbonate, potassium hydrogen carbonate, etc.), alkali-earth metal carbonate (e.g., calcium carbonate, magnesium carbonate, etc.), ammonium carbonate, ammonium hydrogen carbonate, alkali metal phosphate (e.g., trisodium phosphate, tripotassium phosphate, disodium hydrogen phosphate, dipotassium hydrogen phosphate, sodium dihydrogen phosphate, potassium dihydrogen phosphate, etc.), diammonium hydrogen phosphate, ammonium dihydrogen phosphate, alkali-earth metal oxide (e.g., magnesium oxide, calcium oxide, etc.), alkali-earth metal hydroxide (e.g., magnesium hydroxide, calcium hydroxide, etc.) and the like.

Examples of the water-soluble organic acid include citric acid, tartaric acid, malic acid, succinic acid, benzoic acid, chondroitin sulfuric acid, dextran sulfuric acid, carboxymethylcelullose, alginic acid, pectic acid and the like.

Examples of the water-soluble salt of organic acid include alkali metal (e.g., sodium, potassium, etc.) or alkali-earth metal (e.g., calcium, magnesium, etc.) salt of organic acid (e.g., acetic acid, citric acid, tartaric acid, malic acid, succinic acid, benzoic acid, chondroitin sulfuric acid, dextran sulfuric acid, carboxymethylcelullose, alginic acid, pectic acid, etc.) and the like.

Among these, a water-soluble inorganic salt can be advantageously used.

These can be used alone or in combination thereof in a appropriate ratio.

The weight ratio of the water-soluble inorganic salt, organic acid and salt of organic acid to the polymer can be in the range wherein the desired aggregation-preventing effect is obtained. The weight ratio, for example, is about 0.001 to 100 times, preferably about 0.01 to 50 times, more preferably about 0.1 to 10 times the weight of the polymer.

In the present invention, if desired, a microparticle preparation, wherein surfactant is dispersed or coated thereon to give a good dipersibility thereto, can be obtained by (1) spraying a solution containing a surfactant in addition to an inorganic salt, an organic acid or a salt of an organic acid or (2) further spraying a solution containing a surfactant and a solution containing an inorganic salt, an organic acid or a salt of an inorganic acid simultaneously.

Examples of the surfactant include a non-ionic surfactant [e.g., alkyleneglycol (e.g., propylene glycol, etc.), polysorbate (e.g., polysorbate 400, polysorbate 60, polysorbate 80, etc.), Macrogol (e.g., Macrogol 300, Macrogol 400, Macrogol 600, Macrogol 1500, Macrogol 4000, Macrogol 6000, etc.), polyoxyethylene hydrogenated castor oil (e.g., polyoxyethylene hydrogenated castor oil 10, polyoxyethylene hydrogenated castor oil 50, polyoxyethylene hydrogenated castor oil 60, etc.), and so on] and the like.

These can be used alone or in combination thereof in an appropriate ratio.

The weight ratio of the surfactant to the polymer can be in the range wherein the improved dispersibility is obtained. The weight ratio, for example, is about 0.0000001 to 10 times, preferably about 0.000005 to 5 times, more preferably about 0.00001 to 0.01 times the weight of the polymer.

As is mentioned above, microparticle preparation of the present invention can be produced by atomizing and spraying (1) a solution containing a drug a polymer, (2) a dispersion solution in which a part or whole of a drug or polymer is in a state of dispersion, (3) an O/W, W/O, W/O/W or O/W/O type emulsion comprising a solution containing a drug and/or a polymer or (4) and O/W, W/O, W/O/W or O/W/O type emulsion comprising a dispersion solution in which a part or whole of a drug or a polymer is in a state of dispersion from one nozzle of spray dryer and by spraying a solution of a non-adhesive water-soluble inorganic salt, organic acid or salt of organic acid, as a preparation, including microcapsules, from the other nozzle. Further, if desired, it may (I) spray a solution containing a non-ionic surfactant in addition to a water-soluble inorganic salt, a water-soluble organic acid or a water-soluble salt of an organic acid or (2) spray a solution containing a no-ionic surfactant and a solution containing the inorganic salt, organic acid or salt of the inorganic acid simultaneously.

An aqueous solution of the inorganic salt, organic acid or salt of the organic acid can be preferably used.

In the production of the microparticle preparation of the present invention, for example, when a drug is water-soluble, the drug is dissolved in water to prepare an aqueous solution for an internal aqueous phase. As a pH adjustor to maintain the stability or solubility of the water-soluble drug, for example, an inorganic acid (e.g., carbonic acid, phosphoric acid, etc.), an organic acid (e.g., acetic acid, oxalic acid, citric acid, tartaric acid, succinic acid, etc.), alkali metal (e.g., sodium, potassium, etc.) salt of the inorganic acid or organic acid, hydrochloric acid, alkali metal hydroxide (e.g., sodium hydroxide, etc.) and the like can be added to the aqueous solution. Further, as a stabilizer of the water-soluble drug, there can be added, for example, albumin, gelatin, citric acid, sodium ethylenediamine tetraacetate, dextrin, sodium hydrogensulfite or the like. Furthermore, as a preservative, there can be added, for example, paraoxybenzoic acid esters (e.g., methylparaben, propylparaben, etc.), benzyl alcohol, chlorobutanol, thimerosal and the like.

The solution for the internal aqueous phase thus obtained is added to a solution (oil phase) containing the polymer, followed by emulsification to prepare a W/O type emulsion.

As the solution containing the above polymer, a solution of the polymer dissolved in an organic solvent is used.

As the organic solvent, there can be used any solvent whose boiling point is not more than about 120° C. and which is slightly miscible with water and can dissolve the polymer. Examples the organic solvent include halogenated alkanes (e.g., dichloromethane, carbon tetrachloride, etc.), fatty acid ester (e.g., ethyl acetate, butyl acetate, etc.), ethers (e.g., ethyl ether, isopropyl ether, etc.), hydrocarbons (e.g., cyclohexane, n-hexane, pentane, etc.), aromatic hydrocarbons (e.g., benzene, toluene, etc.) and the like. These solvent can be used alone or in combination thereof in an appropriate ratio.

The emulsification can be carried out by dispersion techniques. For example, intermittent shaking, mixing by means of a mixer such as a propeller agitator, tubine agitator or the like, colloid mill operation, mechanical homogenization, ultrasonication and the like may be used.

In the W/O type emulsion, the ratio of the internal aqueous phase to the oil phase depends on a kind of solvent or a particular kind of drug. The preferable ratio of the internal aqueous phase to the oil phase can be in the range of about 5 to 95% (W/W), more preferably about 10 to 30% (W/W).

Alternatively, the drug (which may be water-soluble or fat-soluble) and polymer are dissolved in an organic solvent or a mixture of a solvent miscible with water and water. When the drug is insoluble the mixture is subjected to suspending operation to prepare a S/O type suspension containing finely pulverized drug particles. As the organic solvent in this case, in addition to the aforementioned organic solvents, there can be used solvents readily miscible with water such as acetone acetonitrile, tetrahydrofuran, dioxane, pyridine, alcohols (e.g., methanol, ethanol, etc.) or the like. These solvent can be used alone or in combination thereof in an appropriate ratio. There can be used a mixture having a suitable mixing ratio of water and the above organic solvent. The ratio depends on a kind of solvent or a particular kind of drug. The preferable ratio of the water to the organic solvent can be in the range of about 1 to 99% (V/V), more preferably about 5 to 90% (V/V), most preferably about 10 to 30% (V/V).

Then, the emulsion, suspension, solution or suspended emulsion thus obtained is sprayed into a drying chamber of a spray dryer through a nozzle, and the organic solvent and water in the atomized droplets are removed in an extremely short period of time to prepare powdered microparticle preparation. As the nozzle, a two-liquid type nozzle multi-fluid type nozzle, pressure type nozzle, rotary type nozzle or the like can be used. At the same time, in order to prevent aggregation of the microparticles, an aqueous solution of a water-soluble inorganic acid, organic acid or salt of an organic acid is sprayed from another nozzle. Namely, two nozzles are provided, and the emulsion, suspension, solution or suspended emulsion containing drug and polymer is sprayed from one nozzle, while the aqueous solution of the inorganic salt, organic acid or salt of the organic acid is sprayed from the other nozzle to disperse it on the surface of the microparticles. When a two-liquid type nozzle or pressure type nozzle is used as the nozzle, the two nozzles may be provided in the center of a spray dryer. Preferably, a nozzle having a structure for two-liquid spraying is used so that the solution containing drug and polymer and the aqueous solution of the inorganic salt, organic acid or salt of the organic acid can be sprayed separately without mixing them in the nozzle.

In the above production method, a solution containing a non-ionic surfactant in addition to the inorganic salt, organic acid or salt of the organic acid can be sprayed. Further, a solution containing a non-ionic surfactant and the solution containing the inorganic salt, organic acid or salt of the organic acid can be sprayed from the other separate nozzle simultaneously.

The condition of spraying can be suitably determined according to a kind of microparticle or a kind of spray dryer.

The microparticle preparations thus obtained are subjected to removal of water and the solvent in the microparticle preparations more completely under reduced pressure, if necessary, with warming under reduced pressure.

The particle size of the microparticle preparations depends on the desired degree of prolonged release and a kind of preparation. When the particles is used in a form of a injectable suspension, for example, the particle size can be in the range which satisfies their dispersibility and needle pass requirements. For example, the average diameter is preferably in the range of about 0.5 to 400 μm, more preferably about 2 to 200 μm.

The microparticle preparations of the present invention have many advantages. For example, because the non-adhesive water-soluble inorganic salt, organic acid, salt of the organic acid is dispersed on the surface of the microparticle preparations, aggregation of the microparticle preparation with each other is little in the course of production, and even globular microparticle preparation with can be obtained. When a non-ionic surfactant is used, the microparticle preparations show an excellent dispersibility in a dispersing agent.

Furthermore, according to the process of the present invention, the take-up ratio of the drug into the microparticle preparation can be increased up to the about 100% without any loss of the active component, which is apt to occur in the in-water drying process. Further, the amount of the organic solvent to be used is smaller than that of the in-oil drying process. Furthermore, although it takes an extremely long period of time to remove the solvent in the in-water drying process, this time can be extremely reduced. Thus, the process of the present invention is extremely useful in the industrial production.

The microparticle preparation of the present invention is low toxicity and can be used safely.

The microparticle preparation can be used for treatment or prevention of the various diseases according to a kind of the drug being contained therein. For example, when the drug is a LH-RH derivative, the microparticle preparation can be use for treatment of prostate cancer or endometriosis; when the drug is TRH, the microparticle preparation can be used for treatment of senile dementia or spinal cerebellum degeneration; when the drug is (sulfur-containing alkyl) aminomethylenebisphosphonic acid, the microparticle preparation can be used for treatment or prevention of osteoporosis.

The microparticle preparation of the present invention can be administered as it is into the living bodies as powder formulation, or by molding them in the form of various preparations. Further, the microparticle preparation can be used as raw materials in the production of various preparations.

As the above mentioned preparation, for example, parenteral preparation [e.g., injectable preparation, topical preparation (e.g., nasal preparation, dermatological preparation, etc.), suppositories (e.g., rectal, vaginal), etc.], oral preparation (e.g., powders, granules, capsules, tablets, etc.) and so on can be mentioned. The amount of drug to be included in the preparations depends on the kind of the drug, dosage form, object of treatment, and so on. However, the amount of drug per dosage form may usually be selected from the range of about 0.001 mg to 5 g, preferably about 0.01 mg to 2 g. For example, when the drug is TRH, TRH derivative or a salt thereof, the amount of the drug per dosage form may usually be selected from the range of about 0.1 mg to 1 g, preferably about 1 mg to 500 mg, more preferably about 3 mg to 60 mg.

These preparation can be manufactured by using per se known methods in the field of pharmaceutics.

When the microparticle preparations according to the present invention are to be processed into an injectable preparation, they are dispersed in an aqueous vehicle together with a dispersing agent [e.g., Tween 80 (Astrapowder Co., U.S.A.), HCO 60 (Nikko Chemicals, Japan), carboxymethylcellulose, sodium alginate, etc.], preservative (e.g., methylparaben, propylparaben, benzyl alcohol, chlorobutanol, etc.), isotonizing agent (e.g., sodium chloride, glycerin, sorbitol, glucose, etc.), or the like. The vehicle may also be a vegetable oil (e.g., olive oil, sesame oil, peanut oil, cottonseed oil, corn oil, etc.), propylene glycol or the like. In this manner, an injectable preparation can be produced.

When the microparticle preparations according to the present invention are to be processed into oral preparation, they are mixed with an excipient (e.g., lactose, sucrose, starch, etc.), disintegrating agent (e.g., starch, calcium carbonate, etc.), binder (e.g., starch, gum arabic, carboxymethylcellulose, polyvinylpyrrolidone, hydroxypropylcellulose, etc.) and/or lubricant (e.g., talc, magnesium stearate, polyethyleneglycol 6000, etc.), and the mixtures are compressed in molds, and then if necessary, the preparations may be coated by a per se known method for the purpose of masking of the taste or providing them with enteric or sustained release property. Usable as coating agent are, for example, hydroxypropylmethylcellulose, ethylcellulose, hydroxymethylcellulose, hydroxypropylcellulose, polyoxyethlene glycol, tween 80, Pluornic F86, cellulose acetate phthalate, hydroxypropylmethylcellulose phthalate, hydroxymethylcellulose acetate succinate, Eudragit (Roehm, Germany; methacrylic acid-acrylic acid copolymer) and pigments (e.g., titanium oxide, ferric oxide, etc.).

To manufacture a topical preparation from the microparticle preparations according to the present invention, they are provided in a solid, semi-solid or liquid state in the conventional manner. To manufacture the solid topical preparation for instance, the microparticle preparations either as they are or together with an excipient (e.g., glucose, mannitol, starch, microcrystalline cellulose, etc.) and/or thickner (e.g., natural mucilages, cellulose derivatives, polyacrylates, etc.) are processed into powdery composition. To make a liquid composition, the microparticle preparations are processed into an oily or aqueous suspension in substantially the same manner as in the case of injections. The semi-solid preparation may be an aqueous or oily gel or ointment. In any case, there may be added a pH adjusting agent (e.g., carbonic acid, phosphoric acid, citric acid, hydrochloric acid, sodium hydroxide, etc.), a preservative (e.g., p-hydroxybenzoic acid esters, chlorobutanol, benzalkonium chloride, etc.), or the like.

A suppository of the microparticle preparation according to this invention, whether in oily or aqueous solid or semi-solid state or in liquid state, can be produced in the per se conventional manner. The kind of oleagenous base for such composition is optional as long as it will not dissolve the microparticle preparation. Thus, for example, higher fatty acid glycerides [e.g., cacao butter, Witepsol (Dynamit-Novel, Germany), etc.], intermediate fatty acids [e.g., Miglyol (Dynamit-Novel), etc.] and vegetable oils (e.g., sesame oil, soybean oil, cottonseed oil, etc.) may be mentioned. The aqueous base is exemplified by polyethylene glycol and propylene glycol, while the aqueous gel base may be selected from among natural mucilages, cellulose derivatives, vinyl polymers, polyacrylates, etc.

The dosage of the preparation according to this invention depends on the kind and amount of the active ingredient, dosage form, duration of drug release, recipient animal (e.g., warm blood animals such as mouse, rat, horse, cattle, man), and object of treatment. It is, however, sufficient to ensure that the effective dose of the active ingredient will be administered. The amount per dose to an adult (50 kg weight) may be selected from the range of about 1 mg to 10 g, preferably about 10 mg to 2 g, in terms of the weight of microparticle preparation. For example, in case of microparticle preparation containing TRH, TRH derivative or a salt thereof, the amount per dose to an adult (50 kg weight) may be selected from the range of about 5 mg to 5 g, preferably about 30 mg to 2 g, more preferably about 50 mg to 1 g, in term of the weight of microparticle preparation.

When an injectable dosage form is employed, the volume of the suspension may be selected from the range of about 0.1 ml to 5 ml, preferably about 0.5 ml to 3 ml.

The polymer as a matrix for the microparticle preparation in the present invention can be produced by a per se known method such as a method described in U.S. Pat. Nos. 3,773,919, 4,273,920, 4,675,189, 4,767,628, 4,677,191, 4849,228 or EP-A-481732.

The microparticle preparation of the present invention have, for example, the following characteristics.

(1) The prolonged release of drug in various dosage forms can be ensured. In particular, when a long term treatment with injections is required for the desired effect, the preparation helps achieve the desired pharmaceutical activities stably with an administration schedule of once a week or a month or even a year, instead of giving injections every day. Thus, compared with the conventional sustained release drugs, the prolonged release preparation of the present invention ensure longer sustained effects.

(2) When the injectable preparation is prepared by using the microparticle preparation of the present invention, any surgical operation such as implantation is not required. The preparation can be administered subcutaneously or intramuscularly in quite the same manner as in the conventional injectable suspensions, and it is not required to remove them from the body.

Further, the injectable preparation can be administered directly to the tumor itself, the site of inflammation or the receptor region, so that systemic side effect can be controlled and the drug be allowed to efficiently act on the target organ over a longer period of time, thus making for increased drug efficacy. Furthermore, the injectable preparation can be used in intra-arterial administration in the vascular embolic therapy proposed by Kato et al., of cancer of the kidney and of the lung [Lancet, II, pp.479–480 (1979)].

(3) The release of the active component is continuous and, in the case of hormone antagonists, receptor antagonists or the like, stronger pharmacological activities are obtained than by daily administration.

(4) A drug can be entrapped into the microparticle preparation more efficiently than those obtained by the conventional in-water drying or the W/O/W type three-phase emulsion. Further, a finely pulverized or even globular microparticle preparation can be obtained.

(5) The microparticle preparation having a drug content of 10 to 50% which are hardly obtained by the conventional in-water drying process can be obtained.

(6) Since, compared with the conventional in-water drying process, a solvent removal rate is higher, the hardening rate of the microparticle preparation having a stronger structure can be obtained. Therefore, the excess initial drug release rate after administration can be reduced.

(7) Aggregation and adhesion of the microparticle preparation is remarkably diminished compared with spraying a solution containing only the drug and the polymer.

(8) It is possible to produce microparticle preparations while preventing aggregation of the microcapsules to each other and adhesion of the microparticle preparations to a spray dryer or to a pipe part thereof by spraying the suspension or solution of a water-soluble inorganic salt, a water-soluble organic acid or a water-soluble salt of an organic acid as agent for preventing aggregation of the microparticle preparation at a time while spraying the solution containing the drug and the polymer.

(9) Further, it is possible to produce microparticle preparations having good dispersibility to a dispersing agent by further spraying a solution containing a non-ionic surfactant at a time while spraying the solution containing the drug and the polymer.

The following experiments and examples further illustrate the present invention, but are not to be construed to limit the scope thereof. All percents representing the concentration are weight/volume percents (W/V %) unless otherwise stated.

Experiment 1

Leuprorelin acetate (5 g) was dissolved in water (50 mL) at 60° C. To this solution was added a solution of lactic acid-glycolic acid copolymer [lactic acid/glycolic acid: 75/25 (mole/mole), weight-average molecular weight in terms of polystyrene: 13000] (45 g) dissolved in methylene chloride (75 mL). The mixture was emulsified with a small-size homogenizer (Polytron, manufactured by Kinematica, Switzerland) to obtain a W/O type emulsion.

(1) In-water drying process (the conventional method, hereinafter referred to as "A" process)

The above W/O type emulsion was converted into a (W/O)/W type emulsion in 0.5% polyvinyl alcohol (PVA) aqueous solution (2000 mL) by using homogenizer. Then the emulsion was stirred slowly for 3 hours with a conventional propeller agitator. As methylene chloride was removed, (W/O) type microcapsules were collected by centrifugation. At the same time, the microcapsules were washed with purified water. The collected microcapsules were subjected to freeze-drying a whole day (24 hours) to obtain powder.

(2) Spray drying process (this invention, herein after referred to as "B" method)

The above W/O type emulsion was sprayed from one nozzle of a two-fluid nozzle, of which the inside nozzle diameter for liquid is 2 mm and the outside nozzle diameter for the air is 4 mm, respectively, the air pressure for the outside nozzle being around 2.5 kg/cm$^2$, at a flow rate 10 mL/min. and at the same time, 2% aqueous sodium chloride solution was sprayed from the other nozzle at a flow rate 10 mL/min. into a drying chamber of a spray dryer to obtain microcapsules as powder. The temperature at the entrance of the drying chamber was 95° C., the temperature at the outlet was 40° C. and the air flow was 80 Kg/hr.

Various properties of the microcapsules produced by A and B processes were compared. The results are shown in Table 1.

TABLE 1

Comparison of Propertied of Microcapsules

| Process | Surface state | Drug take-up[1] (%) | Released amount for 1 day[2] (%) | Distribution of particle size[3] (μm) |
|---|---|---|---|---|
| A | many pores | 5.3 | 78 | 5 to 200 |
| B | few | 99 | 24 | 5 to 40 |

1) Drug take-up was determined as follows.
The leuprorelin acetate in the microcapsules was determined by a high performance liquid chromatography (HPLC) procedure using Hitachi L-6300 equipment (Hitachi, Japan). Microcapsules (50 mg) were dissolved in a mixture of dichloromethane (10 ml) and 1/30 M phosphate buffer (pH: 6.0, 20 ml), and leuprorelin acetate extracted into buffer was assayed by an HPLC procedure with an ultra violet (UV) detector under the following conditions; column: Lichrosolb RP.18, 250 mm in length with 4 mm i.d.
column temperature: 30° C.
mobile phase: a mixture of 0.25 acetonitrile (100 ml) and methyl alcohol (150 ml)
flow rate: 0.7 ml/minute
wave length: 280 nm.
Drug take-up was calculated from the following formula:

$$\text{Drug Take-up (\%)} = \frac{\text{The leuprorelin acetate in the microparticles}}{\text{Initial amount of leuprorelin acetate added into microparticles}} \times 100$$

2) Released amount for 1 day (%) was determined as follows.
The microcapsules (50 mg) were suspended in the release medium (10 ml) consisting of 1/30 M phosphate buffer (pH 7), containing 0.05% Tween-80 (Kao-Atlas, Tokyo) in a shaking bottle. This was shaken at 37° C. for one day by using a shaker (Taiyo Scientific Industrial Co., Tokyo).
The residual leuprorelin acetate in the microcapsules was determined after filtering the microcapsules through a 0.8 μm Millipore filter by the analytical method mentioned in 1).
Released amount for 1 day (%) was determined by the following formula.

$$\text{Released amount for 1 day (\%)} = \left( 1 - \frac{\text{The residual leuprorelin acetate in the microparticles}}{\text{The initial amount of leuprorelin acetate in the microparticles}} \right) \times 100$$

3) The distribution of particle size (μm) was determined as follows.
Microcapsules (10 mg) were suspended in Isoton II solution (Nikkaki Ltd., Japan). This suspension was subjected Multilizer (Coulter Inc. Co., U.S.A.) which was equipped with aperture tube of 100 μm or 280 μm to determine the distribution of particle size of the microcapsules.
As shown in Table 1, when surface of the microcapsules was observed with a scanning electron microscope, many pores were observed on the surface of the microcapsules produced by "A" process, whereas pores were hardly observed on the surface of the microcapsules produced by "B" process and sodium chloride was evenly dispersed on the durface of the microcapsules. The take-up of the drug, i.e., leuprorelin acetate, was larger in "B" process the in "A" process. The amount of initially released drug for 1 day (an initial burst) in a release test of the microcapsules ontained by "B" process was larger than that obtained by "A" process.

TABLE 1-continued

Comparison of Propertied of Microcapsules

| Process | Surface state | Drug take-up[1] (%) | Released amount for 1 day[2] (%) | Distribution of particle size[3] (μm) |
|---|---|---|---|---|

The particle size distribution of the microcapsules obtained by "B" process was sharper than that obtained by "A" process. The time required for the production was about 24 hours in "A" process, while it was extremely short and about 10 minutes in "B" process. Thus, in view of the overall comparison, "B" process is an extremely useful production process of microcapsules than "A" process.

Experiment 2

Thyrotropin-releasing hormone (TRH) (0.5 g) and lactic acid-glycolic acid copolymer [lactic acid/glycolic acid: 75/25 (mole/mole), weight-average molecular weight: 14000] (9.5 g) were dissolved homogeneously in a mixture of acetone (30 mL) and water (2 mL). The solution was sprayed from one nozzle of two-fluid nozzles set in the center of the spray dryer at a flow rate 10 mL/min and , at the same time 4% aqueous solution of sorbitol, as an agent for preventing aggregation of the microcapsules, was sprayed from the other nozzle to give microcapsules as powder (hereinafter referred to as C process). Further, in the C process, instead of 4% aqueous solution of sorbitol, 3% aqueous solution of sodium chloride was sprayed as an agent for preventing aggregation of the microcapsule to give microcapsules powder hereinafter referred to as D process). Furthermore, in the C process, instead of 4% aqueous solution of sorbitol, 3% aqueous solution of sodium chloride containing 0.00054% polysorbate 80 was sprayed to give microcapsules as powder (hereinafter referred to as E process).

Various properties of the microcapsules produced by C, D and E process were compared. The results are shown in Table 2.

TABLE 2

Comparison of Propertied of Microcapsules

| Process | Drug take-up (%) | Released amount for 1 day (%) | Distribution of particle size (μm) | Remaining water (%) |
|---|---|---|---|---|
| C | 99 | 6 | 5 to 90 | 0.9 |
| D | 100 | 5 | 5 to 40 | 0.3 |
| E | 100 | 6 | 5 to 40 | 0.3 |

In any one of C, D and E processes, the take-up of the TRH was almost equally high (99 to 100%). In any one of microcapsules obtained by C, D and E process, the amount of released drug for 1 day in a release test in 1/30M phosphate buffer (pH 7.0) at 37° C. was equally small (5 to 6%). The particle size distribution of the microcapsules obtained by D and E method were equal [5 to 40 μm (mean 23 μm) and 5 to 40 μm (mean 24 μm] and were sharper than that obtained by C method [5 to 90 μm (mean 45 μm)]. The remaining water of microcapsules obtained by any one of C, D and E was lower, 0.9%, 0.3% and 0.3%, than that of microcapsules obtained by in-water drying method, 1.0%.

When the surface of the microcapsules obtained by any one of C, D and E process was observed with a scanning electron microscope, pores were hardly observed. The microcapsules obtained by C process slightly adhered each other owing to sorbitol on the their surfaces. This made the particle size distribution of the microcapsules obtained by C process large.

When evaluating the dispersibility of the microcapsules to a dispersing agent containing polysorbate 80 and mannitol, the following results were obtained. The dispersibility of the microcapsules obtained by C process was not good and non-dispersed particles were observed after shaking. After staring for 24 hours, the microcapsules obtained by C process could not be dispersed. The dispersibility of the microcapsules obtained by D process was almost good, but a few non-dispersed particles were still observed and these could be dispersed by ultrasonication. The particles which sedimented after standing for 24 hours could be easily re-dispersed by shaking. The dispersibility of the microcapsules obtained by E process was good. The microcapsules could be easily dispersed, and the particles which sedimented after standing for 24 hours could be easily re-dispersed.

EXAMPLE 1

Thyrotropin-releasing hormone (TRH) (0.4 g) and lactic acid-glycolic acid copolymer [lactic acid/glycolic acid: 75/25 (mole/mole), weight-average molecular weight: 14000] (4.6 g) were dissolved homogeneously in a mixture of methylene chloride (9.5 ml), acetonitrile (10 ml) and ethanol (0.5 ml) or a mixture methylene chloride (12 ml), acetonitrile (7.5 ml) and ethanol (0.5 ml). The solution was sprayed from one nozzle of two-fluid nozzles set in the center of the spray dryer at a flow rate of 10 ml/min and, at the same time, 1/5M phosphate buffer (containing disodium phosphate and sodium biphosphate, pH 7.4) was sprayed from the other nozzle for the prevention of aggregation of the microcapsules to give microcapsules as powder. The take-up of the TRH was 100% in each method. The amount of released TRH for 1 day in a release test of the microcapsules obtained by the above method was 15%. The dispersibility of the microcapsules was good. The average particle size of the microcapsules was 22 μm.

EXAMPLE 2

Thyrotropin-releasing hormone (TRH) (0.8 g) and lactic acid-glycolic acid copolymer [lactic acid/glycolic acid: 75/25 (mole/mole), weight-average molecular weight: 14000] (9.2 g) were dissolved homogeneously in a mixture of acetonitrile (34.6 ml) and water (5.3 ml). The solution was sprayed from one nozzle of two-fluid nozzles set in the center of the spray dryer at a flow rate of 10 ml/min and, at the same time, 1/5M phosphate buffer (containing disodium phosphate and sodium biphosphate, pH 7.4) was sprayed from the other nozzle for the prevention of aggregation of the microcapsules to give microcapsules as powder. The take-up of the TRH was 100% in each method. The amount of released TRH for 1 day in a release test of the microcapsules obtained by the above method was 10%. The dispersibility of the microcapsules was good. The average particle size of the microcapsules was 23 μm.

EXAMPLE 3

Thyrotropin-releasing hormone (TRH) (1.6 g) and lactic acid-glycolic acid copolymer [lactic acid/glycolic acid: 75/25 (mole/mole), weight-average molecular weight: 14000] (18.4 g) were dissolved homogeneously in a mixture of acetonitrile (50 ml) and water (10 ml). The solution was sprayed from one nozzle of two-fluid nozzles set in the center of the spray dryer at a flow rate of 10 ml/min and, at the same time, 1/30M phosphate buffer (containing disodium phosphate and sodium biphosphate, pH 7.4) was sprayed from the other nozzle for the prevention of aggregation of the microcapsules to give microcapsules as powder. The take-up of the TRH was 100% in each method. The amount of released TRH for 1 day in a release test of the microcapsules obtained by the above method was 10%. The dispersibility of the microcapsules was good. The average particle size of the microcapsules was 22 μm.

EXAMPLE 4

Thyrotropin-releasing hormone (TRH) (0.8 g) and lactic acid-glycolic acid copolymer [lactic acid/glycolic acid: 75/25 (mole/mole), weight-average molecular weight: 14000] (9.2 g) were dissolved homogeneously in a mixture of methylene chloride (24 ml), ethanol (14 ml) and water (2 ml). The solution was sprayed from one nozzle of two-fluid nozzles set in the center of the spray dryer at a flow rate of 10 ml/min and, at the same time, a mixture of $\frac{1}{10}$M phosphate buffer (containing disodium phosphate and sodium biphosphate, pH 7.4) and $\frac{1}{5}$M aqueous sodium chloride solution was sprayed from the other nozzle for the prevention of aggregation of the microcapsules to give microcapsules as powder. The take-up of the TRH was 100% in each method. The amount of released TRH for 1 day in a release test of the microcapsules obtained by the above method was 18%. The dispersibility of the microcapsules was good. The average particle size of the microcapsules was 23 μm.

EXAMPLE 5

Thyrotropin-releasing hormone (TRH) (0.8 g) and lactic acid-glycolic acid copolymer [lactic acid/glycolic acid: 75/25 (mole/mole), weight-average molecular weight: 14000] (9.2 g) were dissolved homogeneously in a mixture of methylene chloride (10.6 ml), acetonitrile (25.5 ml) and water (3.9 ml). The solution was sprayed from one nozzle of two-fluid nozzles set in the center of the spray dryer at a flow rate of 10 ml/min and, at the same time, $\frac{1}{5}$M phosphate buffer (containing disodium phosphate and sodium biphosphate, pH 7.4) was sprayed from the other nozzle for the prevention of aggregation of the microcapsules to give microcapsules as powder. The take-up of the TRH was 100% in each method. The amount of released TRH for 1 day in a release test of the microcapsules obtained by the above method was 18%. The dispersibility of the microcapsules was good. The average particle size of the microcapsules was 23 μm.

EXAMPLE 6

Cefotiam dihyrochloride (1 g) was dissolved in water (3 ml). To a solution of polylactic acid (weight-average molecular weight: 21000) (9 g) in methylene chloride (20 ml) was added the above solution, and the mixture was emulsified with a small-sized homogenizer (Polytron, Kinematica, Switerland) for 20 seconds. The resulting emulsion was sprayed from inner nozzle of the rotary disc having two-fluid nozzles, at the same time 3% aqueous sodium biphosphate solution containing 0.0001% polyoxyethylene hardened castor oil 60 was sprayed from outer nozzle to give the microcapsules as powder.

EXAMPLE 7

Bleomycin hydrochloride (1 g) and lactic acid-glycolic acid copolymer [lactic acid/glycolic acid: 50/50 (mole/mole), weight-average molecular weight: 10000] (9 g) were dissolved in a mixture of water (5 ml), acetonitrile (30 ml) and ethanol (5 ml). The solution was sprayed from inner nozzle of three-fluid nozzles for two-liquid spraying, at the same time, 2% aqueous sodium bicarbonate solution was sprayed from middle nozzle and air was flowed from outer nozzle to give microcapsules.

According to the present invention, the microparticle preparation having a high drug content, which are hardly obtained by the conventional in-water drying process can be continuously produced in a short time and on a large scale. According to the present invention, because the non-adhesive substance is dispersed on the surface of the microparticle preparations, aggregation and adhesion of the microparticle preparation is remarkably diminished compared with the conventional spray-drying method. Furthermore, it is possible to extremely improve a dispersibility of microparticle preparations by dispersing or coating the surface of the microparticle preparations with a non-ionic surfactant.

What is claimed is:

1. A method for producing a microparticle preparation which comprises spraying a solution of polymer containing a drug and a solution of a water-soluble inorganic salt, a water-soluble organic acid or a water-soluble salt of an organic acid separately from different nozzles and contacting the solution sprays with each other in a spray dryer to produce microparticles of the polymer which contains the drug and are coated at least partially or wholly with the water-soluble inorganic salt, the water-soluble organic acid or the water-soluble salt of the organic acid, wherein the organic acid is selected from the group consisting of citric acid, tartaric acid, malic acid, succinic acid, benzoic acid, chondroitin sulfuric acid, alginic acid and peptic acid, and wherein the polymer is a poly fatty acid ester selected from the group consisting of homopolymers of α-hydroxycarboxylic acid, copolymers of two or more α-hydroxycarboxylic acid, and a mixture thereof.

2. The method according to claim 1, wherein the solution of polymer containing the drug is a homogeneous solution.

3. The method according to claim 1, wherein the solution of polymer containing the drug is a dispersion solution in which a part or whole of the drug or the polymer is in a state of dispersion.

4. The method according to claim 1, wherein the solution of polymer containing the drug is an O/W, W/O, W/O/W or O/W/O emulsion comprising a solution containing the drug and/or the polymer.

5. The method according to claim 1, wherein the solution of polymer containing the drug is an O/W, W/O, W/O/W or O/W/O emulsion comprising a dispersion solution in which a part or whole of the drug or the polymer is in a state of dispersion.

6. The method according to claim 1, wherein the polymer has a weight-average molecular weight of about 3,000 to 30,000.

7. The method according to claim 1, wherein the polymer has a dispersity of about 1.2 to 4.0.

8. The method according to claim 1, wherein the homopolymer of α-hydroxycarboxylic acid is polylactic acid.

9. The method according to claim 1, wherein the copolymer of two or more α-hydroxycarboxylic acid is selected from the group consisting of copolymer of lactic acid/glycolic acid and copolymer of 2-hydroxybutyric acid/glycolic acid.

10. The method according to claim 1, wherein the mixture is a mixture of polylactic acid and copolymer of 2-hydroxybutyric acid/glycolic acid.

11. The method according to claim 1, wherein the drug is a member selected from the group consisting of peptides having biological activities, antibiotics, antitumor agent, antipyretics, analgesics, anti-inflammatory agents, antitussive expectorants, sedatives, muscle relaxants, antiepiliptic agents, antiulcer agents, antidepressants, antiallergic agents, cardiotonics, antiarrhythmic agents, vasodilators, hypotensive diuretics, antidiabetic, anticoagulants, hemostatics, antituberculous agents, hormones agents, narcotic antagonists, bone resorption inhibitors and angiogenesis inhibiting substance.

12. The method according to claim 1, wherein the drug is a water-soluble drug having an n-octanol/water partition coefficient of not more than 1.

13. The method according to claim 1, wherein the drug is a member selected from the group consisting of thyrotropin-releasing hormone and their salts.

14. The method according to claim 1, wherein the water-soluble inorganic salt, the water-soluble organic acid and the water-soluble salt of the organic acid are water-soluble materials which are applicable to human and are solid at about 15° to 25° C. and are non-adhesive in their dried state.

15. The method according to claim 1, wherein the water-soluble inorganic salt is a member selected from the group consisting of halogenated alkali metals, halogenated alkali-earth metals, halogenated ammoniums, alkali metal carbonates, alkali metal hydrogen carbonates, alkali-earth metal carbonates, ammonium carbonate, ammonium hydrogencarbonate, alkali metal phosphates, diammonium hydrogen phosphate, ammonium dihydrogen phosphate, alkali-earth metal oxide and alkali-earth metal hydroxide.

16. The method according to claim 1, wherein the water-soluble salt of the organic acid is a member selected from the group consisting of alkali metal salts of organic acids and alkali-earth metal salts of organic acids.

17. The method according to claim 1, wherein the amount of the water-soluble inorganic salt, the water-soluble organic acid or the water-soluble salt of the organic acid is about 0.001 to 100 times the weight of the polymer.

18. The method according to claim 1, wherein the particle size of the microparticle preparation is about 0.5 to 400 µm.

19. The method according to claim 1, wherein the microparticle preparation is a microcapsule.

20. The method according to claim 1, wherein the solution of the water-soluble inorganic salt, the water-soluble organic acid or the water-soluble salt of the organic acid is an aqueous solution.

21. The method according to claim 1, wherein the solution of the water-soluble inorganic salt, the water-soluble organic acid or the water-soluble salt of the organic acid contains a surfactant.

22. The method according to claim 21, wherein the surfactant is a non-ionic surfactant.

23. The method according to claim 1, wherein a solution of surfactant is sprayed separately from different nozzle and is contacted it with the solution of polymer containing the drug and the solution of the water-soluble inorganic salt, the water-soluble organic acid or the water-soluble salt of the organic acid in the spray dryer.

24. The method according to claim 23, wherein the surfactant is a non-ionic surfactant.

25. A method for producing a microparticle preparation which comprises spraying (a) a solution of a lactic acid/glycolic acid copolymer containing a drug selected from the group consisting of leuprorelin acetate and thyrotropin-releasing hormone and (b) a solution of a water-soluble inorganic salt separately from different nozzles and contacting them with each other in a spray dryer to produce microparticles of the copolymer which contain the drug and are coated at least partially or wholly with the water-soluble inorganic salt.

26. The method of claim 25, wherein the drug is leuprorelin acetate.

27. The method of claim 25, wherein the drug is thyrotropin-releasing hormone.

28. The method according to claim 1, wherein the drug is a drug having a thyrotropin releasing effect.

* * * * *